United States Patent [19]

Klotzsche et al.

[11] Patent Number: 5,681,878

[45] Date of Patent: Oct. 28, 1997

[54] LOW-DUSTING PULVERULENT HYDROPHILIC POLYMERS

[75] Inventors: Helmut Klotzsche, Alzenau; Gustav Remmel, Gelnhausen; Ulrich Riegel, Frankfurt am Main; Uwe Stüven, Bad Soden, all of Germany

[73] Assignee: Cassella Aktiengesellschaft, Germany

[21] Appl. No.: 424,658

[22] Filed: Apr. 19, 1995

[30] Foreign Application Priority Data

Apr. 22, 1994 [DE] Germany ............... 44 14 117.3

[51] Int. Cl.$^6$ ............................................. C08K 5/24
[52] U.S. Cl. ................... 524/269; 524/306; 524/307; 524/310; 524/311
[58] Field of Search ................... 524/269, 306, 524/307, 310, 311

[56] References Cited

U.S. PATENT DOCUMENTS 4,080,358  3/1978  Krumel et al. .
4,732,968  3/1988  Obayashi et al. ............ 528/490
4,748,215  5/1988  Lindner et al. ............... 524/457
5,087,656  2/1992  Yoshinaga et al. ............ 524/493
5,096,944  3/1992  Tomiju et al. .

FOREIGN PATENT DOCUMENTS 96790     12/1983  European Pat. Off. .
0224923    6/1987  European Pat. Off. .
0509708   10/1992  European Pat. Off. .
2646430   11/1990  France .
94/22940  10/1994  WIPO .

Primary Examiner—Jeffrey T. Smith
Attorney, Agent, or Firm—Connolly & Hutz

[57] ABSTRACT

The present invention relates to pulverulent water-swellable hydrophilic (co)polymers which comprise, for reducing dusting, auxiliaries from the series consisting of silicones and/or other auxiliaries, the latter in a total amount of less than 1% by weight, for example polyglycols or polyglycol ethers, the vapor pressure of the individual auxiliaries being not more than 0.1 mbar at 20° C. and their melting point being not more than 100° C., processes for their preparation and their use for absorption of water and aqueous solutions.

20 Claims, No Drawings

LOW-DUSTING PULVERULENT HYDROPHILIC POLYMERS

The present invention relates to pulverulent water-swellable hydrophilic polymers such as are employed, for example for the absorption of water and aqueous solutions, in particular body fluids such as blood and urine, to which have been added, to reduce dusting, one or more auxiliaries, the vapour pressures of which are not more than 0.1 mbar at 20° C. and the melting points of which are not more than 100° C.

Such water-absorbing polymers, which are often also called super-absorbers, are known per se from numerous publications. Modified naturally occurring polymers and partly or fully synthetic polymers are employed. The fully synthetic polymers are as a rule prepared by free radical polymerization of various hydrophilic monomers in aqueous solution by various methods. In general, crosslinking agents are polymerized into the polymers, which means that the resulting polymer is no longer water-soluble but only water-swellable. Super-absorbers which can be used are, for example, polymers based on (meth)acrylic acid, which are partly present in neutralized form as alkali metal salts.

The super-absorber polymer is as a rule comminuted mechanically, dried and ground. The pulverulent water-swellable polymer is obtained by this process in a more or less wide particle size spectrum, depending on the preparation process. A typical particle size spectrum for a water-swellable fully synthetic polymer ground after drying is in the range from 10 to 900 µm, of which the particle size fraction from 100 to 850 µm is employed as the absorption material for practical processes. In spite of sieving off over a screen cover having a mesh size of 150 µm and removal of the fine dust having a particle size of up to about 150 µm, under technical conditions, residual fractions of fine dust having a particle size of less than 100 µm can still remain to the extent of 1%, and those having a particle size of less than 10 µm can still remain to the extent of 0.5%, in the products intended for use as an absorption material. Fine dust having a particle size of less than 10 µm is undesirable for reasons for inhalation toxicology. Fine dust contents of less than 100 µm cause visually detectable dust with all its secondary symptoms and lead to handling problems in the production and processing plant, and are therefore likewise undesirable.

The treatment of particulate substances to reduce or suppress dusting is known per se from numerous publications. For example, Czechoslovakian Patent Specification CS B-237 182 describes the addition of 2 to 5% of various auxiliaries to tannins to prevent dust, Japanese Patent Application JPA-03/247644 describes the addition of 0.2 to 2.0 parts of silicone oil to polyvinyl chloride, Japanese Patent Application JPA-01/271485 describes spraying of polyether-modified silicone oils onto solid fuels such as, for example, coal, Finnish Patent FI-B-85387 describes the treatment of mineral wool products with polymeric anti-dusting agents such as, for example, polyvinyl acetate, European Patent Application EP-A-570881 describes the preparation of low-dust granules by application of a solution or suspension of a hydrate-forming substance such as, for example, sodium sulphate, while German Offenlegungsschriften DE-A-28 45 975 and DE-A-30 48 940 describe the treatment of perlites with silicone oils for hydrophobization for their use as oil absorbents and to prevent dusting. In all these cases, however, the substances which are treated with various auxiliaries to prevent or reduce dusting are not water-swellable hydrophilic polymers.

WO-A-90/09236 describes binders for liquids which comprise super-absorbers and—to avoid dusting—also polyethylene glycols; these are mixtures of super-absorbers with inorganic or organic compounds having a large surface area and/or capillary and/or fibrous structure, to which a relatively large amount of polyethylene glycol is added, for example, 20% of polyethylene glycol, based on the weight of the super-absorber polymer. Partly and fully synthetic absorbents to which polyethers (polyethylene glycols, polypropylene glycols, polyethylene oxide/polypropylene oxide block polymers) or hydrocarbons, fatty alcohols, fatty acids or fatty acid esters are added to improve blood dispersibility and blood wettability are described in DE-A-28 44 956 or EP-B-9977, but here also, especially in the case of fully synthetic absorbents based on polyacrylic acid, relatively large amounts of the auxiliaries are added; nothing is reported here, however, of a reduction in dusting. The agglomeration of pulverulent water-swellable polymers to prevent blocking and to improve the rate of liquid uptake is described in DE-A-37 41 157 and 37 41 158, but this is the agglomeration of exclusively fine-particled polymer, for example that having more than 90% by weight of a particle size fraction below 90 µm. The agglomeration of polymer particles having an average particle diameter of 0.1 to 15 µm with certain polyalkylene glycol derivatives is disclosed in WO-A-92/13912. A process for the conversion of likewise exclusively extremely fine powders of water-swellable polymers, for example powders having a particle size of less than 100 µm, into a useable form is described in DE-A-40 21 847, although this process, which comprises carrying out a polymerization reaction, is expensive.

The object of the present invention is to provide pulverulent water-swellable hydrophilic polymers which are employed as absorption material in practice in an easily obtainable form which does not have the disadvantages caused by the fine dust, but has the same good performance and processing properties.

Surprisingly, it has now been found that such absorption materials are obtainable by adding to pulverulent water-swellable polymers small amounts of certain auxiliaries by means of which the fine and extremely fine dust particles are bonded permanently to the coarser particles of the polymer in the sense of agglomeration and/or sticking.

The present invention relates to a pulverulent water-swellable hydrophilic (co)polymer, characterized in that, to reduce dusting, the powder comprises one or more auxiliaries from the series consisting of silicones and/or one or more other auxiliaries, the latter in a total amount of less than 1% by weight, based on the Weight of the (co)polymer powder, from the series consisting of fatty alcohols, fatty alcohol esters, fatty acids, fatty acid esters, fatty acid amides, sulphated fatty acid amides and esters, sulphosuccinic esters, polyols, polyethers, polyglycols, polyglycol ethers, aliphatic hydrocarbons and paraffin oils, the vapour pressure of the individual auxiliaries being not more than 0.1 mbar at 20° C. and their melting point being not more than 100° C.

Possible water-swellable hydrophilic (co)polymers are naturally occurring, partly synthetic and fully synthetic substances. Partly synthetic and fully synthetic substances are preferred, in particular anionic (co)polymers based on (meth)acrylic acid, which are present in partly neutralized form as alkali metal salts, in particular sodium and/or potassium salts. The polymers can be homo- and copolymers, which are obtainable from acrylic acid and/or methacrylic acid alone, from these monomers together with one or more other monomers or from one or more other monomers alone, but also, for example, grafted anionic (co)polymers, for example based on (meth)acrylic acid, present in partly neutralized form as an alkali metal salt, for example graft polymers on starch or cellulose or polysaccharides or derivatives thereof or on polyalkylene oxides, such as polyethylene oxides or polypropylene oxides. If polyalkylene oxides that is to say polymers of ethylene oxide and/or propylene oxide, are the graft base, these can also be, for example, etherified or esterified, for example they can be present as di-maleic acid half-esters. The polymers can thus be, for example, those described in EP-A-316 792 or EP-A-400 283. The content of these patent applications is expressly also a constituent of the present disclosure.

Examples which may be mentioned of monomers which can be used, in addition to (meth)acrylic acid, in the preparation of the polymers are (meth)acrylic acid methyl, ethyl and hydroxyalkyl esters, (meth)acrylamide, crotonic acid, maleic and fumaric acid, itaconic acid, 2-acrylamido-2-methylpropanesulphonic acid, vinylsulphonic acid and vinylphosphonic acid, and the methyl, ethyl and hydroxyalkyl esters and amides of these acids, esters and amides of all the acids mentioned containing amino and ammonium groups and water-soluble N-vinylamides, and units originating from all other monomers customary in the preparation of super-absorber polymers can also be contained in the polymer. The polymer is preferably crosslinked. Examples which may be mentioned of suitable crosslinker substances which can be employed in the preparation of super-absorber polymers and contain two or more olefinic double bonds and the structural elements of which can then be contained in the (co)polymer are methylenebis(meth)acrylamide, bisacrylamidoacetic acid, esters of unsaturated acids of polyols, for example ethylene glycol di(meth)acrylate or trimethylolpropane triacrylate or allyl compounds, such as, for example allyl (meth)acrylate, polyallyl esters, tetraallyloxyethane, triallylamine, tetraallylethylenediamine or allyl esters of phosphoric acid, as well as vinylphosphonic acid derivatives, such as are described, for example, in EP-A-343 427. The content of crosslinking agents, which are already added during preparation of the super-absorber polymers, is preferably 0 to 20% by weight, particularly preferably 0 to 3% by weight, based on the total monomers employed. The (co)polymer is otherwise prepared by methods which are known per se, such as are described, for example, in EP-A-400 283, preferably by polymerization in aqueous solution by the process of so-called gel polymerization. The super-absorber polymers can also be post-crosslinked in the aqueous gel phase in a manner which is known per se.

The comminution, drying and grinding of the super-absorber polymer, that is to say the preparation of the (co)polymer powder which is to be improved according to the invention in respect of its dust formation, are also carried out by methods which are known per se. The super-absorber polymer particles obtained by grinding can also be crosslinked on the surface. The low-dust (co)polymer powders according to the invention are preferably polymers which are crosslinked on the surface. Substances which are suitable for such surface crosslinking are, for example, compounds which contain two or more groups which can form covalent bonds with the carboxyl groups of the hydrophilic polymer. Suitable compounds are, for example, di- and polyglycidyl compounds, such as phosphonic acid diglycidyl esters, alkoxysilyl compounds, polyaziridines, polyamines or polyamidoamines, it being possible for the compounds mentioned also to be used as mixtures with one another (see, for example, EP-A-83 022, EP-A-543 303 and EP-A-530 438). Polyamidoamines which are suitable as crosslinking agents are described, in particular, in EP-A-935. The content of the abovementioned patent applications is also expressly a constituent of the present disclosure.

Super-absorber (co)polymer powders which comprise, for reducing dusting, auxiliaries which have a particle size distribution suitable for the intended use, that is to say, for example, contain up to 50–100% of the particle size fraction from 100 to 850 μm, preferably 70–100%, particularly preferably 90–100% of this particle size fraction, are preferably prepared from such powders obtained by grinding.

The auxiliaries which the (co)polymer powders according to the invention comprise for reducing dusting can be liquid or solid at room temperature. Auxiliaries which are present as a liquid at room temperature are preferred.

The (co)polymer powders according to the invention preferably comprise silicones. Suitable auxiliaries from the series of silicones are, for example, polysiloxanes, in which methyl, ethyl, propyl or phenyl groups, or else several of these radicals at the same time, are contained as organic radicals. Preferred compounds are polydimethylsiloxanes and polymethylphenylsiloxanes, particularly preferably polydimethylsiloxanes. The polysiloxanes can be chain-like and cyclic polymers, preferably those having a linear structure, in particular polydimethylsiloxanes having a linear structure. It is furthermore preferable to employ the silicones or polysiloxanes in the form of their commercially available products, which are usually a mixture of substances and can also be modified silicones. Preferred commercially available liquid silicones are the products generally called silicone oils, and in particular in turn silicone oils based on polydimethylsiloxane, specifically having a linear structure. Preferred compounds are, finally, siloxanes having a viscosity at 25° C. of 5 to 20,000 cSt, particularly preferably those of 50 to 350 cSt, especially preferably those of 80 to 120 cSt, specifically those of about 100 cSt.

Examples of other auxiliaries which the (co)polymers according to the invention can comprise to reduce dusting, by themselves or as a mixture of several of these substances, if desired also in addition to one or more silicones, in a total amount of less than 1% by weight, based on the weight of the (co)polymer powder, are hexadecanol, octadecanol, hexadecyl acetate, octadecyl acetate, palmitic acid, stearic acid, palmitic acid methyl ester, stearic acid methyl ester, sulphosuccinic acid diisooctyl ester in the form of its sodium salt, hexylene glycol, 2-methyl-2,4-pentanediol, octamethylene glycol, octadecane, eicosane, commercially available paraffin oils and paraffins, which can comprise, for example, paraffinic, naphthenic and aromatic hydrocarbons, having a melting point of not more than 100° C. and a vapour pressure of not more than 0.1 mbar at 20° C.

Preferred other auxiliaries, which do not belong to the silicones, for reducing dusting are polyglycols and their derivatives, in particular polyalkylene glycols and polyalkylene glycol ethers, above all the mono- and dialkyl ethers. Polyethylene glycols, polypropylene glycols, ethylene oxide/propylene oxide copolymers, in particular block polymers, polyethylene glycol and polypropylene glycol mono- and di-($C_1$–$C_4$)alkyl ethers, in particular methyl ethers, and also polyglycol ethers of higher molecular weight fatty alcohols, having a molecular weight are particularly preferred on the basis of which the requirements of vapour pressure and melting point are met. It is in turn preferable to employ the polyglycols and polyglycol ethers in the form of commercially available products, which are usually a mixture of various substances, in particular those having various molecular weights.

The desired reduction in dusting of the super-absorber powders is already achieved when very low amounts of the stated auxiliaries are employed. If the (co)polymer powder comprises silicone as auxiliaries, it can also comprise these in an amount of, for example, up to 5% by weight, based on the weight of the (co)polymer, without considerable adverse changes in other pro-perties of the powder. The powder preferably comprises silicones in a total amount of 0.005 to 5.0% by weight, particularly preferably 0.01 to 5.0% by weight, most particularly preferably 0.01 to 1.0% by weight, in each case based on the weight of the (co)polymer powder. If the powder comprises one or more other auxiliaries—by themselves or together with silicones—for reducing dust, the total amount of these other auxiliaries, based on the weight of the (co)polymer powder, is preferably 0.01 to 0.95% by weight, particularly preferably 0.05 to 0.7% by weight, especially preferably 0.05 to 0.5% by weight.

The preparation of the co(polymer) powder with reduced dusting can be carried out in a manner which is known per se, for example by mixing the super-absorber powder intimately and as homogeneously as possible with the auxiliary or auxiliaries, if desired also simultaneously with other auxiliaries for other purposes, for example substances which are suitable for the abovementioned surface crosslinking. Mixing can be carried out in a continuous or batchwise procedure in any apparatus suitable for mixing pulverulent products with solid or liquid additives, for example in a tumbler mixer. It is preferable to prepare the pulverulent water-swellable hydrophile (co)polymer with reduced dusting by charging the (co)polymer with the auxiliary or auxiliaries in liquid form or with a liquid solution or dispersion of the auxiliary or auxiliaries. The liquid auxiliary or auxiliaries or the liquid solution or dispersion of the auxiliary or auxiliaries is thereby added uniformly, preferably sprayed on, to the super-absorber powder and is mixed intimately with this. This can be effective, for example, in a Peterson-Kelly mixer or, for example, by the process described in EP-A-534 228. If the auxiliary or auxiliaries is or are added in the form of a solution, it is preferable to distil off the solvent again after mixing, i.e. to carry out a drying operation again. Suitable solvents for charging the powder with the auxiliaries for reducing dusting are, for example, alcohols, such as, for example, methanol, isopropanol or propane-1,2-diol, ketones, such as, for example, methyl ethyl ketone, or esters, such as ethyl acetate or n-, iso-, sec- and tert-butylacetate. The (co)polymer is preferably charged with the auxiliary or auxiliaries in the temperature range from 0° C. to 100° C., particularly preferably in the range from 10° C. to 80° C., especially preferably in the range from 20° C. to 40° C.

However, the present invention also relates generally to a process for reducing dusting of pulverulent water-swellable hydrophilic (co)polymers, characterized in that the powder is charged with one or more auxiliaries from the series consisting of silicones and/or with one or more other auxiliaries, the latter in a total amount of less than 1% by weight, based on the weight of the (co)polymer powder, from the series consisting of fatty alcohols, fatty alcohol esters, fatty acids, fatty acid esters, fatty acid amides, sulphated fatty acid amides and esters, sulphosuccinic esters, polyols, polyethers, polyglycols, polyglycol ethers, aliphatic hydrocarbons and paraffin oils, the vapour pressure of the individual auxiliaries being not more than 0.1 mbar at 20° C. and their melting point being not more than 100° C. Preferred embodiments of this process are the variants of the invention described above as preferred.

The present invention furthermore relates to the use of substances from the series consisting of silicones, by themselves or as mixtures, as auxiliaries for reducing dusting of pulverulent water-swellable hydrophilic (co)polymers and to the use, by themselves or as a mixture and in a total amount of less than 1% by weight, based on the weight of (co)polymer powder, of substances from the series consisting of fatty alcohols, fatty alcohol esters, fatty acids, fatty acid esters, fatty acid amides, sulphated fatty acid amides and esters, sulphosuccinic esters, polyols, polyethers, polyglycols, polyglycol ethers, aliphatic hydrocarbons and paraffin oils as auxiliaries for reducing dusting of pulverulent water-swellable hydrophilic (co)polymers, the vapour pressure of individual substances used in this way being not more than 0.1 mbar at 20° C. and their melting point being not more than 100° C. Here also, preferred variants of this use are those which correspond to the variants of the invention described above as preferred.

In the nature, according to the invention, of dust binding in pulverulent water-swellable hydrophilic (co)polymers, this effect is already achieved in an outstanding manner when low amounts of the auxiliaries are employed. Amounts employed of 0.05 or 0.1% by weight, usually amounts of less than 0.5% by weight, based on the weight of the (co)polymer powder, are often already sufficient to achieve the desired reduction in the very fine dust or fine dust content in the super-absorber and, for example, to solve the handling problems in the production and processing plant, so that the exhaust expenditure can be reduced there in an inexpensive manner. These low amounts of auxiliaries for reducing dusting in general cause no deterioration in other properties of the super-absorber powders, for example a decrease in flow properties or a decrease in bulk density. In principle, however, a decrease in, for example, the bulk density and the flow pro-perties of super-absorber powders which is undesirable for many intended uses is observed to a varying extent when relatively large amounts of the auxiliaries are employed, a factor which depends, for example, on the auxiliary, on the (co)polymer and on the mixing process. Known super-absorber mixtures which comprise larger amounts of corresponding auxiliaries for achieving the effects sought therein often have such disadvantages.

It is particularly surprising that as a rule not only an efficient binding of dust is achieved even when such a small amount of the auxiliaries is employed, with which, for example, the bulk density properties of the product are not adversely changed, but that super-absorber powders to which silicones have been added as auxiliaries for reducing dusting even have a higher bulk density, which is probably to be attributed to deaeration of the space between the polymer particles and a higher packing density thereby achieved in the polymer powder. In the case of the polydimethylsiloxanes preferred as auxiliaries, especially those having a linear structure, and quite specifically in the case of those having a viscosity of 50 to 350 cSt at 25° C., for example about 100 cSt at 25° C., not only is no significant decrease in the bulk density properties recorded, but in contrast an increase in the bulk density is recorded beyond the binding of dust already achieved when very small amounts are employed, for example when amounts of 5% are employed.

The pulverulent water-swellable hydrophilic (co) polymers according to the invention comprising auxiliaries for reducing dusting can be used for all purposes for which such super-absorbers are usually employed, in particular, that is to say, for absorption of water and aqueous solutions. They are preferably used for absorption of body fluids, in particular blood and urine. For this purpose, they are incorporated, in articular, into absorbent disposable hygiene articles, for example into nappies, tampons or sanitary towels, or for other medical purposes Other intended uses are, for example, those as water-retaining soil-improving agents or as moisture-binding agents in cable sheathing.

EXAMPLES

The abbreviations given in the examples have the following meanings:

PEG: Polyethylene glycol having an average molecular weight corresponding to the number stated Methylpolyethylene glycol having an average molecular weight corresponding to the number stated MTG: Methyltriethylene glycol HEXG: Hexylene glycol (2-methyl-2,4-pentanediol)

PAFF: Industrial paraffin oil ®PIONIER 2024, commercial pro-duct from Hansen & Rosenthal, Hamburg (®PIONIER is a registered trade mark of Hansen & Rosenthal)

SILI: Polydimethylsiloxane, commercial product of Bayer AG with the trade name ®BAYSILONE M 100 (®BAYSILONE is a registered trade mark of Bayer AG)

GENA: Ethylene oxide/propylene oxide block polymer, commercial product of Hoechst AG with the trade name ®GENAPOL PF 40 (®GENAPOL is a registered trade mark of Hoechst AG)

SUCC: Sodium salt of sulphosuccinic acid diisooctylester, 70% strength by weight, dissolved in 1,2-propanediol

Example 1

0.25 g of polyethylene glycol of average molecular weight 300 was added to 500 g of the pulverulent water-swellable polymer commercially obtainable under the trade name ®SANWET IM 5000 S (®SANWET is a registered trade mark of Sanyo Chemical Industries) from Hoechst AG/Cassella AG, and the components were homogeneously mixed in a bottle on a rolling device by continuous uniform rolling for 4 hours. The fine dust content in the resulting super-absorber powder and in the untreated starting polymer powder is shown in Table 1.

The dust contents were determined by a laser particle size analyser by the dry dispersion method after prior sieving out of particles having a particle size of greater than 250 μm, i.e. sieving off over a sieve of mesh size 250 μm. However, this determination method is suitable only for relative measurements for comparison purposes, since, because of the measurement methodology, it gives values which are too high for the lower particle sizes. By the dispersion operation, the sample is subjected to high shear stresses, which means that abrasion and comminution of larger particles occurs.

Examples 2 to 15

Super-absorber powders according to the invention with reduced dusting were prepared analogously to Example 1 with further auxiliaries and other amounts of auxiliaries. The polymers, auxiliaries, amounts employed and fine dust contents are shown in Table 1.

TABLE 1

| Example | Polymer | Auxiliary Type | Amount[1] (%) | Fine dust content[2] (%) |
|---|---|---|---|---|
| — | ®SANWET IM 5000 S | — | — | 0.095[3] |
| 1 | ®SANWET IM 5000 S | PEG 300 | 0.05 | 0.078[3] |
| 2 | ®SANWET IM 5000 S | " | 0.1 | 0.074[3] |
| 3 | ®SANWET IM 5000 S | " | 0.3 | 0.062[3] |
| 4 | ®SANWET IM 5000 S | " | 0.5 | 0.004[3] |
| 5 | ®SANWET IM 5000 S | MPG 350 | 0.1 | 0.073[3] |
| 6 | ®SANWET IM 5000 S | " | 0.3 | 0.068[3] |
| 7 | ®SANWET IM 5000 S | " | 1.0 | 0.019[3] |
| — | SANWET VS 3790 | — | — | 0.34[4] |
| 8 | SANWET VS 3790 | HEXG | 0.05 | 0.28[4] |
| 9 | SANWET VS 3790 | " | 0.07 | 0.15[4] |
| 10 | SANWET VS 3790 | " | 0.1 | 0.18[4] |
| 11 | SANWET VS 3790 | MTG | 0.05 | 0.28[4] |
| 12 | SANWET VS 3790 | " | 0.07 | 0.24[4] |
| 13 | SANWET VS 3790 | " | 0.1 | 0.21[4] |
| 14 | SANWET VS 3790 | PAFF | 0.01 | 0.31[4] |
| 15 | SANWET VS 3790 | " | 0.5 | 0.19[4] |

[1] Amount employed in percent by weight, based on the weight of polymer employed.
[2] Content of fine dust having a particle size of less than 10 μm in the super-absorber powder, stated in percent by weight
[3] Determined by the dry dispersion method.
[4] Determined by the dry dispersion method as for [3], but in these cases the products per se were measured directly without the particle size fraction greater than 250 μm being sieved off. The results are reproducible and are suitable for comparison purposes, but in absolute terms are too imprecise, since the measurement range is exceeded because the particles are too large.

Examples 16 to 25

The polymer was prepared in accordance with the following instructions:

4950 g of demineralized water/ice were initially introduced into a polyethylene vessel having a capacity of 10 l and well insulated by foamed, plastic material, 553 g of sodium bicarbonate was suspended therein, and 1986 g of acrylic acid were slowly metered in such that foaming-over of the reaction solution was avoided, this solution cooling to a temperature of about 5°–3° C. 1.5 g of a polyethylene glycol 300-di-maleic acid half-ester, and 4.7 g of tetraallyloxyethane, 2.7 g of methylenebisacrylamide, 3.9 g of sorbitan monolaurate and 22 g of urea were added. The initiators, a redox system comprising 1.7 g of 2,2'-azobisamidinopropane dihydrochloride, dissolved in 20 g of demineralized water, 3.9 g of potassium peroxodisulphate, dissolved in 150 g of demineralized water, and 0.33 g of ascorbic acid, dissolved in 20 g of demineralized water, were added in succession at a temperature of 4° C. and the components were mixed thoroughly. The reaction solution was then left to stand, without stirring, a solid gel forming as a result of the polymerization which ensues, in the course of which the temperature rose to about 85° C., and the gel was then comminuted mechanically, 970 g of 50% strength sodium hydroxide solution were added (degree of neutralization of the acrylic acid=73 mol %), the mixture was thoroughly kneaded twice, 212 g of a commercially available polyamidoamine diluted to 5% and based on adipic acid, diethylenetriamine, ethylenediamine and ethanolamine, which had been reacted with epichlorohydrin and had been subjected to alkali/amine treatment, were added, and the mixture was again thoroughly kneaded twice and then dried at temperatures above 150° C. in a stream of air, ground and sieved.

In each case 400 g of this polymer powder were initially introduced into a 1 l laboratory tumbler mixer. After the auxiliaries shown in Table 2 had been added in the amounts stated therein, the mixture was tumbled for two hours and the fine dust contents were determined by the dry dispersion method.

TABLE 2

| Example | Auxiliary | | Fine dust |
|---|---|---|---|
| | Type | Amount[1] (%) | content[2] (%) |
| — untreated | — | — | 0.885[4] |
| 16 | SILI | 0.005 | 0.852[4] |
| 17 | " | 0.03 | 0.700[4] |
| 18 | " | 0.5 | 0.625[4] |
| 19 | " | 1.0 | 0.475[4] |
| 20 | " | 2.0 | 0.335[4] |
| 21 | " | 3.0 | 0.276[4] |
| 22 | " | 4.0 | 0.266[4] |
| 23 | " | 5.0 | 0.260[4] |
| 24 | GENA | 0.5 | 0.730[4] |
| 25 | SUCC | 0.5 | 0.440[4] |

[1], [2], [4] = see Table 1

Examples 26 to 30

In an industrial scale vibratory mixer, the auxiliaries were metered into the super-absorber polymer via the screws during the mixing operation and the mixing operation was continued until the mixture was homogeneous (for the polymer, auxiliary and amounts, see Table 3). The dust content was determined by the "falling method" in a D.P.A. dust separator from Roaches (recommended for determination of the dust content according to the document ISO/TC 38/SC 1-N 646). This method results in more accurate values in respect of the ease of release of the fine dust particles. In this method, a certain amount of the pulverulent product falls from a certain height into a container. After a defined period of time, the dust formed is suctioned off under controlled vacuum conditions and fed to a laser analyser. The measurement results are shown in Table 3.

TABLE 3

| Example | Polymer | Auxiliary | | Fine dust content[5] |
|---|---|---|---|---|
| | | Type | Amount[1] (%) | (ppm) |
| — | SANWET IM 5000 SG | — | — | 121 |
| 26 | SANWET IM 5000 SG | PEG 300 | 0.1 | 2 |
| — | SANWET IM 3900 G | — | — | 74 |
| 27 | SANWET IM 3900 G | PEG 300 | 0.05 | 5 |
| 28 | SANWET IM 3900 G | SILI | 0.05 | 2 |
| 29 | SANWET IM 3900 G | SILI + PEG 300 | 0.005 + 0.03 | 3 |
| 30 | SANWET IM 3900 G | SILI + PAFF | 0.03 + 0.05 | 3 |

[1] = see Table 1
[5] Content of the fine dust with a particle size less than 10 μm in the super-absorber powder, stated in mg of fine dust/kg of product per se (= ppm)

We claim:

1. Pulverulent water-swellable hydrophilic (co)polymer powder, comprising a water-swellable hydrophilic (co) polymer powder physically mixed with one or more auxiliaries wherein said auxiliaries comprise silicone(s) wherein the vapor pressure of the individual auxiliary being not more than about 0.1 mbar at about 20° C. and having a melting point being not more than about 100° C.

2. The (co)polymer powder according to claim 1, wherein the (co)polymer is an anionic (co)polymer based on (meth) acrylic acid present in partly neutralized form as an alkali metal salt.

3. The (co)polymer powder according to claim 1, wherein the (co)polymer is a grafted anionic (co)polymer based on (meth)acrylic acid present in partly neutralized form as an alkali metal salt.

4. The (co)polymer powder according to claim 1, wherein said auxiliaries are polysiloxanes.

5. The (co)polymer powder according to claim 1, wherein said polysiloxanes are polydimethylsiloxanes having a linear structure and having a viscosity at 25° C. of about 50 to about 350 Cst.

6. The (co)polymer powder according to claim 1, wherein said polydimethylsiloxanes are silicone oils having a viscosity at 25° C. of about 80 to 120 Cst.

7. The (co)polymer powder according to claim 1, further comprising at most in a total amount of about 1% by weight, based on the weight of the (co)polymer powder, one or more different auxiliaries other than silicone selected from the group consisting of fatty alcohols, fatty alcohol esters, fatty acids, fatty acid esters, fatty acid amides, sulphated fatty acid amides and esters, sulphosuccinic esters, polyols, polyethers, polyglycols, polyglycol ethers, aliphatic hydrocarbons and paraffin oils, the vapor pressure of the individual auxiliaries being not more than about 0.1 mbar at about 20° C. and their melting point being not more than about 100° C.

8. The (co)polymer powder according to claim 1, wherein said auxiliaries are selected from the group consisting of polyethylene glycols, polypropylene glycols, ethylene oxide/propylene oxide block polymers, polyethylene glycol mono-($C_1$–$C_4$)alkyl ethers, polyethylene glycol di-($C_1$–$C_4$) alkyl ethers, polypropylene glycol mono-($C_1$–$C_4$)alkyl ethers and polypropylene glycol di-($C_1$–$C_4$)alkyl ethers.

9. The (co)polymer powder according to claim 1, wherein said auxiliaries are silicones in a total amount of 0.005 to 5.0% by weight.

10. The (co)polymer powder according to claim 1, wherein said auxiliaries are silicones in a total amount of 0.01 to 1% by weight.

11. The (co)polymer powder according to claim 1, wherein the polymer is crosslinked by a crosslinking agent.

12. The (co)polymer powder according to claim 1, wherein said crosslinking agent is present in an amount up to 20% by weight.

13. The (co)polymer powder according to claim 1, wherein said (co)polymer is crosslinked on the surface.

14. The (co)polymer powder according to claim 13, wherein the (co)polymer is crosslinked on the surface by compounds which contain two or more groups which form covalent bonds with the carboxyl group of the hydrophilic polymer.

15. The (co)polymer powder according to claim 14, wherein said compounds which contain two or more groups are selected from the group consisting of diglycidyl, polyglycidyl, polyaziridine, polyamine and polyamidoamine.

16. A process for the preparation of a pulverulent water-swellable hydrophilic (co)polymer with reduced dusting according to claim 1, comprising charging the (co)polymer is with an auxiliary or auxiliaries in liquid form or with a liquid solution or dispersion of the auxiliary or auxiliaries.

17. The process according to claim 16, wherein the charging of the (co)polymer with the auxiliary or auxiliaries takes place in a temperature range from about 0° C. to about 100° C.

18. The process according to claim 17, wherein the temperature range is from about 10° C. to about 80° C.

19. The process according to claim 18 wherein the temperature range is from about 20° C. to about 40° C.

20. An absorbent comprising water-swellable hydrophilic (co)polymers according to claim 1.

* * * * *